United States Patent [19]

Gibson et al.

[11] Patent Number: 5,130,456
[45] Date of Patent: Jul. 14, 1992

[54] BIS(REISSERT COMPOUNDS) FROM REACTION OF MONOALDEHYDE, MONOAMINE AND DIACID HALIDE

[75] Inventors: Harry W. Gibson; Yajnanarayana H. R. Jois, both of Blacksburg, Va.

[73] Assignee: Virginia Tech Intellectual Properties, Inc., Blacksburg, Va.

[21] Appl. No.: 685,380

[22] Filed: Apr. 15, 1991

Related U.S. Application Data

[63] Continuation-in-part of Ser. No. 418,067, Oct. 6, 1989, Pat. No. 5,041,601.

[51] Int. Cl.$^5$ .................. C07C 255/04; C07C 255/17; C07C 255/40
[52] U.S. Cl. .................... 558/445; 558/392; 558/393
[58] Field of Search .................... 558/392, 393, 445

[56] References Cited

U.S. PATENT DOCUMENTS

| | | | |
|---|---|---|---|
| 3,923,494 | 12/1975 | Teach | 558/445 X |
| 3,932,168 | 1/1976 | Stein et al. | 558/392 X |
| 3,966,789 | 6/1976 | Oishi et al. | 558/445 |
| 4,740,228 | 4/1988 | Kis-Tamas et al. | 548/540 X |
| 4,785,019 | 11/1988 | Moore | 558/392 X |
| 4,929,713 | 5/1990 | Gibson et al. | 528/230 |

FOREIGN PATENT DOCUMENTS

| | | | |
|---|---|---|---|
| 2016453 | 1/1987 | Japan | 558/392 |
| 2177394 | 1/1987 | United Kingdom | 558/392 |

OTHER PUBLICATIONS

Gibson et al.; Amer. Chem. Soc., Polymer Preprints, 2a(1), pp. 154–155, (1988).
Pandya et al., Amer. Chem. Soc., Polymer Preprints, 30(1), pp. 206–207, (1989).
Gibson et al.; Amer. Chem. Soc., Polymer Preprints, 30(1), pp. 208–209, (1989).
McEwen et al., J. Org. Chem. (1980), 45, pp. 1301–1308.
C.A., 87:202161k, Voznesenskaya, et al. (1977).
Rappoport–Editor, "The Chemistry of the Cyano Group", (1970), p. 76, Interscience Pub., N.Y.-London.
Weygand/Hilgetag, "Preparative Organic Chemistry", (1972), p. 519, John Wiley & Sons, N.Y.

Primary Examiner—Joseph Paul Brust
Attorney, Agent, or Firm—Richard P. Fennelly; Louis A. Morris

[57] ABSTRACT

A bis Reissert can be formed by the initial reaction of an aliphatic or aromatic aldehyde (e.g., propionaldehyde) and primary amine (e.g., methylamine) to form a reaction product which is then reacted with a diacid chloride (e.g., adipoyl chloride).

5 Claims, No Drawings

BIS(REISSERT COMPOUNDS) FROM REACTION OF MONOALDEHYDE, MONOAMINE AND DIACID HALIDE

This is a continuation-in-part of pending U.S. Ser. No. 418,067, filed Oct. 6, 1989, now U.S. Pat. No. 5,041,601.

BACKGROUND OF THE INVENTION

Recently, it has been proposed that Reissert compounds be synthesized to develop novel heterocyclic polymers for high performance applications (see H. W. Gibson et al., Amer. Chem. Soc., Polymer Preprints, 29(1), 154, 1988). Bis (Reissert compounds) have been synthesized in excellent yields by the use of a trimethylsilyl cyanide reagent and can be used to develop such polymers (see A. Pandya et al., Amer. Chem. Soc., Polymer Preprints, 30(1), 206, 1989).

W. E. McEwen et al., in J. Org. Chem. 1980, 45, 1301-1308 discuss the synthetic uses of open-chain analogues of Reissert compounds by first preparing an aminonitrile by condensation of a primary monoamine with a cyanohydrin followed by reaction of the aminonitrile with an acid chloride to form the Reissert compound.

U.S. Ser. No. 418,067, filed Oct. 6, 1989, describes the formation of bis(Reissert) compounds by the reaction of a dialdehyde, a monoamine and a monoacid chloride.

DESCRIPTION OF THE INVENTION

The instant invention relates to the formation of an open chain bis Reissert product of the reaction product of a monoaldehyde, a monoamine, and a diacid chloride by: (a) the reaction of a monoaldehyde, e.g., propionaldehyde, with a primary amine, e.g., methylamine, in the presence of cyanide and bisulfite to yield a reaction product thereof; and (b) the reaction of the reaction product from (a) with a diacid halide, e.g., a diacid chloride, to yield the bis Reissert product thereof.

The initial reaction of the instant process involves the reaction of a monoaldehyde (e.g., propionaldehyde) of the formula $$R—C(O)H$$

where R is aliphatic or aromatic with a primary amine $R'NH_2$, where R' is alkyl, e.g., methyl, in the presence of a cyanide source (e.g., an alkali metal cyanide) and a bisulfite source (e.g., an alkali metal bisulfite). The reaction can be conducted at temperatures of from about $-25°$ C. to about $100°$ C. using a molar ratio of the aldehyde to the amine of from about 1:1 to about 1:2.5. The amount of cyanide and bisulfite, respectively, can range from about 1 to about 1.5 moles and from about 1 to about 1.5 moles per mole or reactants, respectively. The resulting reaction product, an alpha aminonitrile, has the formula $$\begin{array}{c} RCHCN \\ | \\ NHR' \end{array} \text{ and}$$

is then used in the following step.

The reaction product described above is then reacted with a diacid halide, e.g., a diacid chloride of the formula $$Cl(O)CR''C(O)Cl$$

where R" is alkylene (e.g., a $C_4$–$C_6$ alkylene group) or arylene to yield the desired bis(Reissert compound) having the following formula:

$$\begin{array}{c} CN \quad\quad\quad CN \\ | \quad\quad\quad\quad | \\ R—CHN(O)CR''C(O)NCH—R \\ | \quad\quad\quad\quad | \\ R' \quad\quad\quad\quad R' \end{array}$$

where R is aliphatic or aromatic and R' and R" are as defined above. This reaction step can be conducted at room temperature in a suitable organic solvent (e.g., dimethylformamide) and base to remove by-product hydrochloric acid.

The instant invention is further understood by the Examples which follow.

EXAMPLE 1

This illustrates preparation of 1-cyano-1-(N-methylamino) propane from propionaldehyde.

A mixture of water (400 ml) and sodium bisulfite (125 gm, 1.2 moles) in a 1L beaker equipped with a mechanical stirrer was stirred until solution was complete. Propanaldehyde (87 ml, 1.2 moles) was added and the mixture was stirred for two hours. Methylamine (101 ml of 40% wt solution, 1.2 moles) was added and stirred for two hours. This was followed by the addition of NaCN (59 gm, 1.2 moles). The reaction mixture was stirred overnight, and the organic layer was separated. The aqueous layer was extracted with dichloromethane (3×150 ml). The organic layers were pooled and washed with water (3×150 ml), dried over $Na_2SO_4$ and concentrated to get the crude product, 80.5 gm (68.4%). Purified product was obtained by vacuum distillation, bp 27-8° C. at 2 mm. $^1H$ NMR ($CDCl_3$): δ 3.42 (t, J=6.94 Hz, 1H, CHCN), 2.56 (s, 3H, N-$CH_3$), 1.88–1.72 (dq, 2H, $CH_2$), 1,1 (t, J=7.59 Hz, 3H, $CH_3$).

EXAMPLE 2

This illustrates the formation of adipoyl bis[N-(1-cyanopropyl)-N-methylamide].

To a well stirring solution of 1-cyano-1-(N-methylamino) propane (0.32 mole, 31.42 gm) and triethylamine (0.35 mole, 50 ml) in dry DMF (100 ml) at 10°–15° C., adipoyl chloride (0.16 mole, 29.3 gm) in dry DMF (25 ml) was added over a period of ten minutes. The reaction mixture was stirred for twenty-four hours at room temperature and quenched by pouring into water (2 l) and left stirring overnight. It was then extracted with EtOAc (3×300 ml). The organic layers were pooled, washed with aqueous 8% HCl (3×500 ml), aqueous saturated $NaHCO_3$ (3×500 ml), brine (3×500 ml) and dried over $Na_2SO_4$. The crude product was obtained by rotary evaporation (39.5 gm, 80.5%). The product was purified by silica gel column chromatography eluting with 20% EtOAc in hexanes. The boiling point of this compound (colorless oil) is not reported as it is known to lose HCN at elevated temperature. IR (Neat): 2972, 2939, 2880 (CH), 2239 (CN), 1735, 1654 (CO), 1459, 1400, 1280, 1124 and 1102 cm$^{-1}$. $^1H$ NMR ($CHCl_3$): δ 5.58 (t, 2H, J=8.1 Hz, HCN), 3.04 (s, 6H, $NCH^3$), 2.4 (bs, 4H, $COCH_2$), 2.1–1.6 (m, 8H, $CH_2$ and $CH_2CH_2$), 1.00 (t, 6H, J=7.4 Hz, $CH_3$). Analysis: Calculated for $C_{16}H_{24}N_4O_2$: C 62.71, H 8.55, N 18.29. Found: C 62.54, H 8.59, N 18.21%.

We claim:

1. A bis Reissert compound of the formula
where R is alkyl or aryl, R' is alkyl and R" is alkylene or arylene.
2. A compound as claimed in claim 1 wherein R" is alkylene.
3. A compound as claimed in claim 1 wherein R" is alkylene and R is alkyl.
4. A compound as claimed in claim 1 wherein R" is $C_4$ to $C_6$ alkylene, R' is methyl, and R is alkyl.
5. A compound as claimed in claim 4 wherein R is $C_2H_5$.